US007157562B1

(12) United States Patent
Olsen, II et al.

(10) Patent No.: US 7,157,562 B1
(45) Date of Patent: Jan. 2, 2007

(54) BIOPROCESS FOR THE PRODUCTION OF RECOMBINANT ANTI-BOTULINUM TOXIN ANTIBODY

(75) Inventors: Gilbert G. Olsen, II, Abingdon, MD (US); William E. Bentley, Annapolis, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 543 days.

(21) Appl. No.: 10/414,555

(22) Filed: Apr. 14, 2003

(51) Int. Cl.
*A23J 1/00* (2006.01)
*C07K 1/00* (2006.01)
*C07K 14/00* (2006.01)
*C07K 16/00* (2006.01)

(52) U.S. Cl. ............... 530/414; 530/387.1; 530/388.2; 530/413; 530/866; 530/867

(58) Field of Classification Search ............... None
See application file for complete search history.

(56) References Cited

U.S. PATENT DOCUMENTS

| | | | |
|---|---|---|---|
| 5,756,670 A * | 5/1998 | Guss et al. ............... 530/350 |
| 5,932,449 A * | 8/1999 | Emanuel et al. ........... 435/70.1 |
| 6,284,488 B1 * | 9/2001 | Weir et al. ................. 435/69.1 |
| 6,566,500 B1 * | 5/2003 | Vitetta et al. .............. 530/350 |
| 6,652,857 B1 * | 11/2003 | Williams et al. ........... 424/169.1 |
| 2002/0102613 A1 * | 8/2002 | Hoogenboom ............... 435/7.1 |
| 2002/0155114 A1 * | 10/2002 | Marks et al. ............. 424/150.1 |
| 2004/0175385 A1 * | 9/2004 | Marks et al. ............. 424/164.1 |
| 2004/0219542 A1 * | 11/2004 | Houston et al. ................ 435/6 |
| 2005/0042775 A1 * | 2/2005 | Pomato et al. .............. 436/547 |
| 2006/0160184 A1 * | 7/2006 | Hoogenboom et al. .... 435/69.1 |

FOREIGN PATENT DOCUMENTS

EP        001054018 A1 * 11/2000

OTHER PUBLICATIONS

Crowe, J et al, Qiagen, Inc., Methods in Molecular Biology, vol. 31, 1994, paes 371-387, 6xHis-NiNTA chromatography as a superior technique in recombinant protein expression/purification.*
Lindner, P et al, Methods: A comparison to Methods in Enzymology, vol. 4, pp. 41-56, 1992, Purification of Native proteins from the cytoplasm and periplasm of *Escherichia coli* using IMAC and Histidine tails: A comparison of Proteins and Protocols.*
Schier, R et al, J. Mol. Biol., 1996, pp. 551-567, vol. 263.*
Emanuel, Peter et al, Journal of Immunological Methods, vol. 193(1996) 189-197.*

* cited by examiner

*Primary Examiner*—Mark Navarro
*Assistant Examiner*—Ginny Allen Portner
(74) *Attorney, Agent, or Firm*—Ulysses John Biffoni

(57) ABSTRACT

A process for producing recombinant anti-botulinum toxin antibody comprising the steps of fermenting recombinant *E. Coli* cells in broth, concentrating the cells by removing the broth, crushing the concentrated cells, separating a permeate derived from the crushed cells from cell debris, purifying a recombinant antibotulinum antibody (Fab) from said permeate, and separating said Fab from impurities by diafiltration.

18 Claims, 1 Drawing Sheet

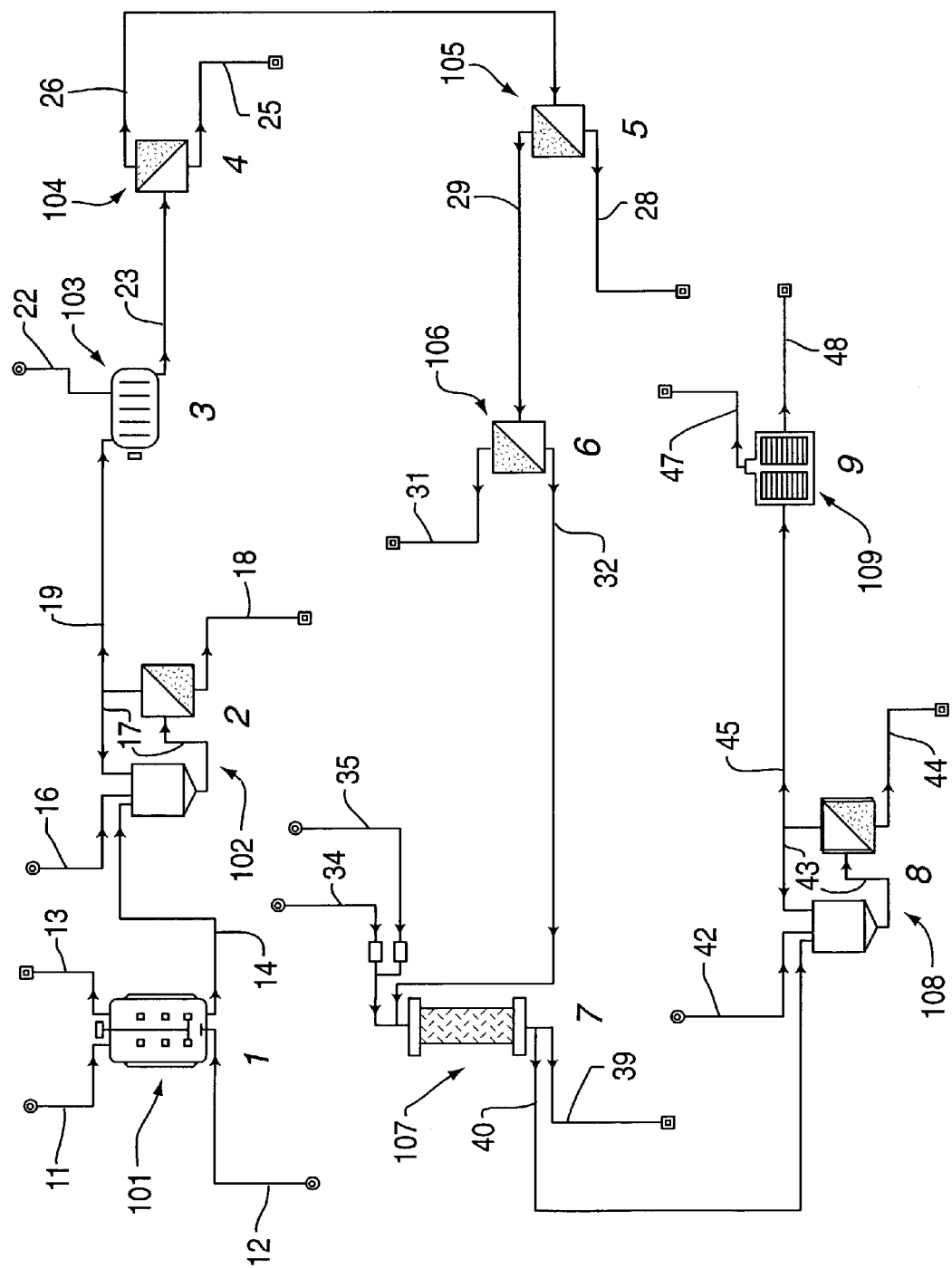

US 7,157,562 B1

BIOPROCESS FOR THE PRODUCTION OF RECOMBINANT ANTI-BOTULINUM TOXIN ANTIBODY

GOVERNMENT INTEREST

The invention described herein may be manufactured, licensed, and used by or for the U.S. Government.

BACKGROUND OF THE INVENTION

1. Field of the Invention

The present invention relates to the production of recombinant antibodies (Fab). More particularly, the Fab is produced in large quantities of high purity and fractions. The present invention provides for the process and resultant composition of the bioprocess for the large-scale production of recombinant anti-botulinum toxin antibody.

2. Brief Description of the Prior Art

Genetic engineering has lead to the creation of recombinant antibodies (Fab) which are similar to monoclonal antibodies. These recombinant proteins can be expressed or replicated in large quantities from their host E. Coli cells. However, effective production of these biomolecules requires a bioprocess which can produce them in sufficient quantity and purity at a minimum cost.

Previously, the anti-botulinum toxin antibody has been produced in bench-scale quantities only. This increases the cost and produces a smaller total yield. Previously known processes for purifying the Fab were generally not amenable to scale-up to larger quantities and did not provide an optimal large-scale process. In general, low yield production significantly impacts on the ability to produce anti-botulinum. Moreover, limitations in the previous known process have restricted the quantity and purity of the Fab production.

In view of the foregoing, improvements in the production of Fab have been desired. In addition to the increase in quantity and purity, a one-column process is desired for the process to further enhance production.

The present invention addresses these needs.

SUMMARY OF THE INVENTION

In view of the foregoing, it is therefore an object of the present invention to provide a process for producing recombinant antibodies in large quantity.

It is a further object of the present invention to provide a process for producing recombinant antibodies in acceptable purity.

These and other objects are achieved by the present invention which includes a process for producing recombinant anti-botulinum toxin antibody comprising the steps of fermenting E. Coli cells in broth, concentrating said cells by removing said broth, crushing said concentrated cells, separating a retentate of said crushed cells from cell debris, and, separating said retentate effective to separate Fab from impurities.

In another aspect of the present invention, there is provided a product of recombinant anti-botulinum toxin antibody from a process of fermenting E. Coli cells in broth; concentrating said cells by removing said broth; crushing said concentrated cells; separating a retentate of said crushed cells from cell debris; adding said retentate to Ni—NTA resin; separating said Ni—NTA with said retentate through a column; and, washing said separated Ni—NTA with said retentate with a solution so as to separate Fab from impurities.

The process and product of the present invention are extremely valuable in the field of producing recombinant antibodies. Other and further advantages of the present invention are set forth in the description and appended claims.

BRIEF DESCRIPTION OF DRAWING

FIG. 1 is schematic illustration for a process for the production of Fab.

DETAILED DESCRIPTION OF THE PREFERRED EMBODIMENTS

The present invention is a process and product from that process for purified Fab. The Fab process allows for large quantities of recombinant anti-botulinum toxin antibody to be produced in a one-column process. The process allows large yields and reliable purity of the final product.

Referring to FIG. 1, a process of the preferred embodiment for the production of anti-botulinum toxin antibody is shown. The process is illustrated for a 150-liter scale process producing a purified concentration of recombinant antibodies (Fab). The process is shown as steps 1–9, which include fermentor step 1, diafilter steps 2 and 8, DYNOMILL step 3, ultrafilter steps 4–6, affinity chromatography step 7 and freezer-dryer step 9, as described below.

In fermentor step 1, 115 liters of Terrific broth (TB), in a concentration of 47 g/L, was placed in a 150-liter fermentor 101 and seeded by adding 2.5 liters of a mixture of E. Coli cells in Terrific Broth at 47 g/L at a feed inlet 11. The E. Coli cells used were genetically engineered such that the DNA of the cells expresses a Bot Fab protein having a polyhistidyl tail attached, said cells being under the transcriptional control of a promoter induced by IPTG. These E. Coli cells are described in U.S. Pat. No. 5,932,449 which is hereby incorporated by reference in its entirety. The fermentor 101 is a steel jacket container filled with water and having an impeller to increase aeration of the contents. Terrific broth is commercially available and contains 11.8 grams of casein digest, 23.6 grams of yeast extract, 9.4 grams of $K_2HPO_4$ and 2.2 grams of $KH_2PO_4$ per liter. Alternatively, Luria Broth (LB), which contains 10 grams of casein digest, 5 grams of yeast extract and 10 grams of sodium chloride per liter, may be used. Carbenicillin, an antibiotic, is then added to the mixture in the fermentor 101 at the feed inlet 11 in a concentration of two mg/ml stock to 1 ml stock carbenicillin/liter broth. The temperature is held at 37° C. to allow the cells to grow as the impeller is rotated to aerate the mixture. An air inlet 12 allows air to enter the fermentor 101, and an air exhaust 13 removes air from the fermentor 101. After the optical density of the cells has risen to approximately 0.7 at 600 nm in 3.5 to 4.5 hours, isopropyl beta-D-thiogalactopyranoside (IPTG) is added. A total of 115 milliliters (ml) of 1.0 M IPTG is added, initially at 40% volume (46 ml), with 30% (34.5 ml) IPTG added each hour thereafter until a final concentration of 1.0 mM is reached in approximately two-hours. The IPTG causes the protein (Fab) to be synthesized over a period of time. The fermentor 101 is operated for approximately 30 hours, after which time the fermentor 101 is harvested and a separate fermentor step 1 is begun as a batch process. The solution of cells leaves the fermentor 101, is shown traveling along process path 14, and into the diafilter 102 in diafilter step 2.

Once the solution arrives at the diafilter 102, the cells are harvested from the solution by removing the broth during diafilter step 2. At diafilter step 2, the solution is diafiltered using a Sonication Buffer Diafiltrate (SB) which enters at inlet 16. The SB includes 50 mM $NaPO_4$ and 300 mM NaCl at a pH of 8.0. An equal amount of buffer volume to amount of concentrated cells is used each time the cells are diafiltered in the diafilter step 2. The solution proceeds through the diafiltration of step 2 five times, which is shown as circular path 17. As the solution travels in the circular path 17, the cells are concentrated to one-fifth their initial volume using two 0.22 um tangential flow membranes (5 $ft^2$ each), reducing the initial 115 liters which entered into the fermentor 101 to approximately 24 liters recovered in the diafilter 102. The diafiltration of step 2 effectively removes the broth proteins in the filtrate from the cells in the retentate by allowing the broth to pass through the membrane as filtrate, while retaining the cells in the membrane. Filtrate is shown being removed from the retentate through process path 18, and the retentate is shown leaving the diafilter 102 through process path 19 and entering a DYNOMILL step 3. Approximately 24 liters of the retentate leaves the diafilter 102 containing approximately 3% broth protein impurities.

In the DYNOMILL step 3, the cells are lysed using a bead mill DYNOMILL 103. The retentate which contains the concentrated cells is pumped into the DYNOMILL 103 at a rate of 5–7 liters/hr, and crushed using glass beads. The cells make three passes through the DYNOMILL 103 in a batch process fashion to ensure that all cells are completely crushed. A solution of phenylmethylsufonyl fluoride (PMSF) is added as shown passing through process path 22 to the crushed cells, until a final retentate mixture concentration of 0.2 mM PMSF is obtained. Addition of the PMSF is done to bind destructive enzymes (proteases) which are released from the crushed cells. The retentate mixture from the DYNOMILL 103 contains a mire of cell debris and product, and approximately 24 liters of retentate mixture leaves the DYNOMILL step 3, shown as passing through process path 23, and then arrives at the ultrafilter step 4.

At ultrafilter step 4, the liquid part of the retentate mixture is separated from the cell debris using a single 0.22 um tangential flow membrane of ultrafilter 104. As the retentate mixture passes through the membrane, the cell debris are trapped by the membrane with the liquid part of the retentate mixture, which is a clarified liquid, passing through the membrane. The cell debris are excluded from the mixture, as shown passing through process path 25, and the clarified liquid is shown as traveling along process path 26 to arrive at the ultrafilter step 5. Alternatively, this step may be done using a centrifuge. In the ultrafilter step 4, the approximately 24 liters of retentate enters and approximately 22 liters of clarified liquid leaves.

At the ultrafilter step 5, the 22 liters of clarified liquid is filtered through a 300,000 nominal molecular weight cutoff tangential flow membrane of ultrafilter 105 to remove fine particles, high molecular weight impurities, and DNA. The fine particles, high molecular weight impurities, and DNA are trapped by the membrane leaving the permeate to flow through the membrane. These removed particles and impurities are discarded, as shown passing through process path 28. The permeate has a volume of approximately 22 liters leaving step 5, and is shown exiting from the ultrafilter 105 through process path 29 to then arrive at ultrafilter step 6.

The permeate is concentrated at ultrafilter step 6 using a 10,000 nominal molecular weight cutoff tangential flow membrane of ultrafilter 106. The ultrafilter 106 separates the low molecular weight impurities of the permeate from the concentrated product. The concentrated product of the permeate in retained in the membrane with the low molecular weight impurities, such as small proteins and liquids, passing through the membrane. The low molecular weight impurities are discarded, as shown passing through process path 31. The concentrated product has an 11 fold concentration effect, going from 22 liters to 2 liters of volume. The 2 liters of concentrated product is shown leaving step 6 along process path 32 and then entering the affinity chromatography step 7. At this point in the process, the concentrated product has been purified to a range of 10,000 Mw (molecular weight) to 300,000 Mw, with the Fab at approximately 50,000 Mw.

In the affinity chromatography step 7, the concentrated product is purified using a large nickel nitrilo-tri-acetic acid (Ni—NTA) column using imidazole gradient. This is done by having the concentrated product added to a Ni—NTA resin in a bottle and rocking the bottle for preferably 2–4 hours, or alternatively overnight, at 4° C., prior to pouring it into the column. The resin/product mixture in the bottle is then poured through the column and the resin is packed. The column is attached to the affinity chromatography system 107. The remaining liquid of the concentrated product is removed using SB carrier as shown arriving through process path 34 as the washing solution. This washing step continues until the absorbance at 280 nm is at a constant minimum. Imidazole is added as shown passing through process paths 35. The Fab is eluted using a gradient of 0 mM to 500 mM imidazole mixed with the SB amount decreasing to zero. Five column volumes of imidazole are used to elute the Fab. The Fab is collected in a fraction collector and active fractions are pooled, in amounts of 8 ml per tube. The Fab product leaves the affinity chromatography step 7 as shown passing through process path 40 and then enters the diafilter step 8, with waste exiting at path 39.

In step 8, the Fab product enters a diafilter 108 where it is dialyzed against phosphate buffered saline (PBS), shown as process path 42, to remove the imidazole in a multi-step filtration. This is shown as circular path 43. One liter of PBS contains 120 mM NaCl, 2.7 mM KCl, 10 mM buffer salt of $KH_2PO_4$ or $K_2HPO_4$, depending on whether the pH is 7.4 or 7.6, respectively, at 25° C. The diafilter 108 has a membrane of 12,000 to 14,000 nominal molecular weight which allows the imidazole to pass through as the Fab is collected. A stir bar is placed in the PBS solution, with the PBS changed 3 separate times, after 1–2 hours, 1–2 hours, and 12 hours. This is done at 4° C. to protect the product from ordinary bacteria. The imidazole waste is removed as shown passing through process path 44. The dialyzed product is shown exiting the diafilter step 8 through process path 45.

The dialyzed product remaining on the membrane from the diafilter step 8 then enters the freeze-dryer step 9. At step 9, the dialyzed Fab is quick frozen with dry ice and ethanol, and freeze-dried in the freeze-dryer 109. Water residue from the freeze-dried product is removed, as shown exiting at process path 47. The final purified product is a yellow-brown pellet of Fab with some salt, and is shown passing through process path 48.

EXAMPLE 1

Five two-liter Erlenmeyer flasks containing 500 ml each of *E. Coli* cells in Terrific broth (TB) are used to seed a 150-liter fermentor. The fermentor is prepared using Terrific broth at a concentration of 47 g/L. Carbenicillin is added at two mg/ml stock, 1 ml stock Carbenicillin/Liter broth. After the optical density (@ 600 nm) of the cells have risen to approximately 0.7, isopropyl beta-D-thiogalactopyranoside (IPTG) is added over a two-hour interval to a final concentration of 1.0 mM. Initially 40% (46 ml) of this volume is added and 30% (34.5 ml) each hour thereafter until the final concentration is reached. The IPTG induces the protein (Fab) to be expressed over time. The fermentor is operated for approximately 30 hours.

The cells are concentrated to one-fifth their initial volume using two 0.22 um tangential flow membranes (5 ft² each). The concentrations are diafiltered using Sonication Buffer (SB, 50 mM Na₃PO₄, 300 mM NaCl, pH 8.0 filtered with 0.22 um) five times. The diafiltration step is performed using a volume of buffer equal to that of the concentrated cells.

The concentrated cells are crushed completely after three passes through a bead mill. To this solution is added phenylmethylsufonyl fluoride (PMSF) to a final concentration of 0.2 mM. The mixture of cell debris and product is separated using a single 0.22 um tangential flow membrane. The clarified product is then filtered through a 300,000 nominal molecular weight cutoff tangential flow membrane to remove fine particles, high molecular weight impurities, and DNA. The permeate from the previous step is concentrated using a 10,000 nominal molecular weight cutoff tangential flow membrane and is then ready for purification.

This solution is added to the Ni—NTA resin in a bottle and then rocked 2–4 hours at 4° C. The resin/product mixture is then poured through a column and the resin is packed. The column is attached to a liquid chromatography system and the remaining liquid is removed using SB as the washing solution. This washing step continues until the absorbency at 280 nm is constant. The Fab is eluted using a gradient of 0 mM to 500 mM imidazole. The product is collected in a fraction collector and active fractions are pooled and dialyzed against SB to remove the imidazole. The dialyzed Fab is quick frozen and freeze-dried for the final purified product. The Fab was produced at 55% purity on average with some fractions of greater than 90%.

EXAMPLE 2

Five two-liter Erlenmeyer flasks containing 500 ml each of *E. Coli* cells in Luria broth (TB) are used to seed a 150-liter fermentor. The fermentor is prepared using Luria broth at a concentration of 25 g/L. Carbenicillin is added at two mg/ml stock, 1 ml stock Carbenicillin/Liter broth. After the optical density (@ 600 nm) of the cells have risen to approximately 0.7, isopropyl beta-D-thiogalactopyranoside (IPTG) is added over a two-hour interval to a final concentration of 1.0 mM. Initially 40% (46 ml) of this volume is added and 30% (34.5 ml) each hour thereafter until the final concentration is reached. The IPTG induces the protein (Fab) to be expressed over time. The fermentor is operated for approximately 30 hours.

The cells are concentrated to one-fifth their initial volume using two 0.22 um tangential flow membranes (5 ft² each). The concentrations are diafiltered using Sonication Buffer (SB, 50 mM Na₃PO₄, 300 mM NaCl, pH 8.0 & filtered with 0.22 um) five times. The diafiltration step is performed using a volume of buffer equal to that of the concentrated cells.

The concentrated cells are crushed completely after three passes through a bead mill. To this solution is added phenylmethylsufonyl fluoride (PMSF) to a final concentration of 0.2 mM. The mixture of cell debris and product is separated using a single 0.22 um tangential flow membrane. The clarified product is then filtered through a 300,000 nominal molecular weight cutoff tangential flow membrane to remove fine particles, high molecular weight impurities and DNA. The permeate from the previous step is concentrated using a 10,000 nominal molecular weight cutoff tangential flow membrane and is then ready for purification.

This solution is added to the Ni—NTA resin in a bottle and then rocked 2–4 hours at 4° C. The resin/product mixture is then poured through a column and the resin is packed. The column is attached to a liquid chromatography system and the remaining liquid is removed using SB as the washing solution. This washing step continues until the absorbance at 280 nm is at a constant minimum. The Fab is eluted using a gradient of 0 mM to 500 mM imidazole. The product is collected in a fraction collector and active fractions are pooled and dialyzed against SB to remove the imidazole. The dialyzed Fab is quick frozen and freeze-dried for the final purified product.

In one run, 358 mg of Fab was recovered using a Luria Broth, showing excellent yield and recovery.

It should be understood that the foregoing summary, detailed description, examples and drawing of the invention are not intended to be limiting, but are only exemplary of the inventive features which are defined in the claims.

What is claimed is:

1. A process for producing recombinant anti-botulinum toxin antibody, comprising the steps of:
   (a) fermenting recombinant *E. Coli* cells in broth, said recombinant *E. Coli* cells comprising DNA encoding anti-botulinum toxin antibody (Fab) proteins having a polyhistidyl tail at an end, said DNA under transcriptional control of a promoter induced by isopropyl beta-D-thiogalactopyranoside (IPTG), said fermenting producing a solution of said cells;
   (b) concentrating said cells by removing said broth from said solution by diafiltration;
   (c) crushing said concentrated cells producing crushed cells, cell debris, and retentate mixture; wherein said crushing comprises lysing the cells by mechanical means;
   (d) separating said retentate mixture from said crushed cells and cell debris, wherein said separating comprises passing said retentate mixture, crushed cells, and cell debris through a tangential flow ultrafiltration membrane;
   (e) separating DNA and other protein impurities from said retentate mixture, wherein said separation comprises passing said retentate mixture through a tangential flow ultrafiltration membrane producing a permeate;
   (f) purifying said recombinant antibotulinum antibody (Fab) from said permeate, wherein said purifying step comprises affinity chromatography, wherein said polyhistidyl tail at an end of said Fab provides a ligand, adding said permeate to a Ni—NTA resin in a bottle and rocking said bottle for at least 2 hours, pouring the resin/permeate mixture into a Ni—NTA affinity chromatography column, washing said column with a sonication buffer until the absorbancy at 280 nm is at a constant minimum, and eluting said Fab with an imidazole gradient of 0 mM to 500 mM producing imidazole eluate;
   (g) separating said Fab from said imidazole eluate by diafiltration;
   (h) quick freezing said Fab, and
   (i) freeze-drying said frozen Fab, said freeze-drying comprising lyophilization for stabilizing said Fab, said Fab comprising a protein product in a final purified, stabilized form.

2. The process of claim 1, wherein said fermenting comprises the steps of adding about 115 liters of a Terrific Broth solution to a fermentor, seeding said fermentor by adding about 2.5 liters of a mixture of said recombinant *E. Coli* cells in Terrific Broth to said fermentor, adding an antibiotic to said fermentor, and, after the optical density of the cells has risen to about 0.7 at 600 nm, adding IPTG to said fermentor until a final concentration of about 1.0 mM is reached.

3. The process of claim 2, wherein said antibiotic comprises carbenicillin.

4. The process of claim 2, wherein said about 115 liters of Terrific Broth solution has a Terrific Broth concentration of about 47 grams per liter, and said Terrific Broth in said 2.5 liter mixture also has a Terrific Broth concentration of about 47 grams per liter.

5. The process of claim 2, wherein said fermentor is maintained at about 37° C.

6. The process of claim 1, wherein said fermenting comprises the steps of adding about 115 liters of a Luria Broth solution to a fermentor, seeding said fermentor by adding about 2.5 liters of a mixture of said recombinant *E. Coli* cells in Luria Broth to said fermentor, adding an antibiotic to said fermentor, and, after the optical density of the cells has risen to about 0.7 at 600 nm, adding IPTG to said fermentor until a final concentration of about 1.0 mM is reached.

7. The process of claim 1, wherein said step of concentrating said cells by diafiltration comprises reducing the volume of said solution of cells to one-fifth their original volume by successive filtration through tangential flow membranes, so that broth proteins are separated from said cells.

8. The process of claim 7, wherein said tangential flow membranes comprise 0.22 μm tangential flow membranes.

9. The process of claim 7, wherein said successive filtration comprises five passes through said tangential flow membranes.

10. The process of claim 7, wherein said concentrating by diafiltration further comprises adding a sonication buffer diafiltrate.

11. The process of claim 1, wherein said crushing by mechanical means comprises passing the cells through a DYNOMILL® (glass bead mill).

12. The process of claim 11, further comprising the step of adding a solution of phenylmethylsufonyl fluoride.

13. The process of claim 1, wherein said separating said permeate step comprises passing said permeate, crushed cells and cell debris through a 0.22 μm tangential flow ultrafiltration membrane.

14. The process of claim 1, wherein said separating DNA and other protein impurities step comprises passing said permeate through a 300,000 molecular weight cutoff tangential flow ultrafiltration membrane.

15. The process of claim 1, wherein during said purifying step said Ni—NTA bottle is maintained at about 4° C.

16. The process of claim 1, wherein during said purifying step five column volumes of imidazole are used to elute said Fab.

17. The process of claim 1, wherein said step of separating said Fab from said imidazole eluate by diafiltration comprises ultrafiltration through a membrane having a 12,000 to 14,000 nominal molecular weight cutoff.

18. The process of claim 1, wherein said step of separating said Fab from said imidazole eluate by diafiltration includes dialyzing against phosphate buffer solution.

* * * * *